United States Patent [19]

Prillwitz et al.

[11] Patent Number: 4,725,436

[45] Date of Patent: Feb. 16, 1988

[54] METHOD FOR CONTROLLING HARMFUL FUNGI IN CEREALS

[76] Inventors: Hans-Georg Prillwitz; Maria-Teresa Schreiber, both of c/o Hoechst Aktiengesellschaft, P.O. Box 80 03 20, D-6230 Frankfurt am Main 80, Fed. Rep. of Germany

[21] Appl. No.: 899,536

[22] Filed: Aug. 22, 1986

[30] Foreign Application Priority Data

Aug. 24, 1985 [DE] Fed. Rep. of Germany ....... 3530340

[51] Int. Cl.$^4$ .......... A01N 63/00

[52] U.S. Cl. .......... 424/93; 435/242; 435/253; 435/261; 435/886

[58] Field of Search .......... 424/93; 435/242, 253, 435/261, 886

[56] References Cited

U.S. PATENT DOCUMENTS 4,595,589 6/1986 Tahvonen .......... 424/93

OTHER PUBLICATIONS

H. Bockmann, Nachrichtenblatt Deutscher Pflanzenschutzdienst, 14, 153-156 (1962).

Biological Abstracts, 3, Ref. No. 819 (1982).

Webster's New Collegiate dictionary, 718 (1979).

*Primary Examiner*—Howard E. Schain

*Attorney, Agent, or Firm*—Curtis, Morris & Safford

[57] ABSTRACT

The invention relates to a method for controlling stem break in cereal plants, wherein the fungus *Pseudocercosporella anguioides* or *Pseudocercosporella aestiva* is applied to the cereal plants their seed or their area of cultivation.

10 Claims, No Drawings

METHOD FOR CONTROLLING HARMFUL FUNGI IN CEREALS

A particular problem in cereal cultivation is so-called stem break, which is caused by certain fungi of the genus Pseudocercosporella. When these fungal diseases occur, destruction of the nutrient-conveying vessels in the cereal stem is observed. In an extreme case, this can lead to rotting of the stem base. This generally results in early lodging of the cereal. Substantial losses of yield may be the consequence in this case.

The frequent use of chemical agents for controling stem break can lead to resistance problems. Fungal strains of the genus Pseudocercosporella may develop which are insensitive to the use of such fungicides.

Surprisingly, it has been found that the fungal species *Pseudocercosporella anguioides* and *P. aestiva* can advantageously be used for controling the stem break pathogen *P. herpotrichoides.*

*P. anguioides* and *P. aestiva* are known, naturally occurring species of fungi. They have been deposited under number CBS No. 496.80 (*P. anguioides*) and CBS No. 497.80 (*P. aestiva*) in the Centralbureau voor Schimmelcultures (CBS), Ooosterstraat, Baarn, The Neatherlands. However, both fungal species can be used, regardless of their origin, i.e. the variants and mutants and all naturally occurring strains can be employed according to the invention. The natural strains are isolated by methods known to the skilled worker, see e.g. H. Bockmann, Nachrichtenblatt Deutscher Pflanzenschutzdienst 14, 153–156 (1962).

The present invention therefore relates to a method for controling stem break in cereal plants, wherein the fungal species *Pseudocercosporella anguioides* or *Pseudocercosporella aestiva* is applied to the cereal plants their seed or their areas of cultivation. *P. anguioides* is preferably employed.

*P. anguioides* and *P. aestiva* are not pathogens of the cereal stem, in contrast of *Pseudocercosporella herpotrichoides* var. herpotrichoides and *Pseudocercosporella herpotrichoides* var. acuformis, which cause stem break.

In contrast to these pathogenic species, *P. anguioides* only populates the leaf sheaths and not the cereal stem, whereas *P. aestiva* occurs on the leaf sheaths and on dead plant tissue of cereals.

When *P. anguioides* or *P. aestiva* are applied in particular in the early vegetation phase of cereal plants, inoculation of the stems by the pathogenic Pseudocercosporella species can surprisingly be greatly restricted or even completely surpressed. In the case of spray application, preferred fields of use are in development stage EC 10 to EC 25 (one-leaf stage to middle of the tillering period). Dressing or soil application is also possible.

*P. anguioides* or *P. aestiva* can be used in particular in the cereal species wheat, barley and rye, preferably in winter wheat, winter barley or winter rye.

The fungal species to be used according to the invention can be obtained as an inoculum from one-spore cultures and multiplied as described by H. Bockmann, Nachrichtenblatt Deutscher Planzenschutzdienst 14 (1962), pages 153–156. They can also be grown by cultivation on suitable substrates, such as cereal grains, straw or other plant materials, or with the aid of conventional solid nutrient media, such as potato dextrose agar (PDA), melt or yeast extract agar, water agar, SNA agar (Joffé medium), etc., if appropriate on suitable carrier materials, such as mica schist (®Vermiculit) or plastics, or on appropriate liquid nutrient media without the addition of agar.

The present invention also relates to crop protection agents which contain *P. anguioides* or *P. aestiva* as mycelia and/or spores in addition to suitable diluents, such as water and/or auxiliaries. The auxiliaries employed can be conventional additives, such as adhesives or emulsifiers.

The fungi can be used as mycelia or in the form of spores (conidia).

The agents according to the invention can be used as wettable powders, emulsifiable concentrates, sprayable solutions, dusting agents, dressings, dispersions, granules or microgranules, in the usual formulations.

To use them, the concentrates in the commercial form are, if appropriate, diluted in a conventional manner, for example with water in the case of wettable powders, emulsifiable concentrates, dispersions and water-dispersible (micro) granules. Dust-like and granulated formulations and dressings are not usually diluted with further inert substances before being used. Mixtures or mixed formulations with fungicidal active ingredients or non-fungicidal active ingredients such as insecticides, acaricides, herbicides, fertilizers or growth regulators, are also possible, and a synergistic increase in the activity may also be achieved in some cases.

*P. anguioides* and *P. aestiva* can also be used for controling the stem break pathogen Rhizoctonia spp. in the stated cereal species.

The application rate for the fungi to be used according to the invention can vary between $5.0\times10^4$ and $6.0\times10^{15}$ colony-forming units per ha, in particular between $1.0\times10^9$ and $1.0\times10^{13}$ colony-forming units per ha. Colony-forming units are understood as being either mycelium fragments, mycelium conglomerates or spores. The application rate of spray liquor per ha can vary between 50 and 600 l/ha. The examples below serve to illustrate the invention.

BIOLOGICAL EXAMPLES

A. Preparation of the inoculum:

(a) The inoculum was obtained from single-spore cultures and multiplied in the manner described by BOCKMANN (1962). For this purpose, 2 ml of conidia suspension were incubated in 18 ml of a 0.8% strength malt solution with the addition of streptomycin (0.05%) for 8–10 days at 18° C. in small conical flasks. Thereafter, inoculation with the freshly obtained mycelium suspension was carried out in 300 ml conical flasks which had already been filled with sterilized, moist, swollen wheat grains. After about 10 days, when the grains were covered with the fungus, they were spread out in thin layers in pricking-out dishes, slightly moistened, and placed out in the open at the beginning of the cool season. After about three weeks, when large amounts of conidia have been observed, the grains were laid out to dry at room temperature. For field inoculation, the wheat grains were washed thoroughly with water for a short time. The spore concentration was adjusted to 300,000 conidia/ml of water.

(b) As described in (a), the inoculum of *P. anguioides* was obtained, and multiplied as described by BOCKMANN. Thereafter SNA agar was inoculated with spores or mycelia of *P. anguioides,* a mixture of *P. anguioides* materials from three different sources being used. The inoculated agar was incubated for three weeks at 15° C. and in black light (UV). The agar was then shaken up with an Ultra-Turrax stirrer and the spore suspension obtained was adjusted to $3\times10^5$ spores/ml.

B. Field trials

EXAMPLE B1

Rye, barley and wheat were sown in fall. Inoculation with *P. anguioides* which had been obtained by method (a) was carried out after about 7 weeks, between the beginning of tillering and the principle tillering stage (development stage 21-25) at a rate of application of water of 400 l/ha (concentration: $3\times10^8$ conidia/l). When milk ripeness was attained (development stage 75) the damage to the cereal plants as a result of stem break was rated.

The result is shown in the table below.

TABLE 1

| Application | Dose Spores/ha | % damage by stem break Barley | Rye | Wheat |
|---|---|---|---|---|
| Not inoculated Control (C) | | 68 | 43 | 35 |
| inoculated with *P. anguioides* | $1.2\times10^{11}$ | 12 | 9 | 12 |

EXAMPLE B2

Barley was sown in fall. Inoculation was effected 29 days later, the *P. anguioides* preparation obtained by method (Ab) being used. The dosages are shown in Table 2. The results below were obtained in two independent trials. Rating was carried out when milk ripeness had been attained (according to BOCKMANN's scheme).

TABLE 2

| Application | Dose Spores/ha | % damage Barley |
|---|---|---|
| Trial 1 | $1.2\times10^{11}$ | 8 |
| Trial 2 | $1.2\times10^{11}$ | 11 |
| Control: | | |
| Trial 1 | — | 42 |
| Trial 2 | — | 64 |

As shown by the resulting values in the tables above, damage to the cereal plants is substantially reduced when *P. anguioides* is employed.

We claim:

1. A method for controling stem break in cereal plants wherein the fungus *Pseudocercosporella anguioides* or *Pseudocercosporella aestiva* is applied to the cereal plants, their seed or their areas of cultivation.

2. A method as claimed in claim 1, wherein *P. anguioides* is applied to the plants, their seed or their areas of cultivation.

3. A method as claimed in claim 1, wherein *P. anguioides* or *P. aestiva* is applied to the plants, their seed or their areas of cultivation at an application rate of $5\times10^4$ to $6\times10^{15}$ colony-forming units per ha.

4. A method as claimed in claim 1, wherein *Pseudocercosporella anguioides* is applied to barley, wheat or rye.

5. A method as claimed in claim 1, wherein *P. anguioides* or *P. aestiva* is applied at an application rate of $1.0\times10^9$ to $1.0\times10^{13}$ colony-forming units per ha.

6. A method as claimed in claim 1, wherein *P. aestiva* is applied to the plants, their seed or their areas of cultivation.

7. A method as claimed in claim 1, wherein *P. anguioides* or *P. aestiva* is used to control the stem break pathogen Rhizoctonia spp. or *P. herpotrichoides.*

8. A method as claimed in claim 7, wherein the cereal plants are winter wheat, winter barley or winter rye.

9. A composition for controlling stem break in cereal plants comprising a carrier and an amount of *P. anguioides* or *P. aestiva* effective to suppress stem break in cereal plants.

10. A composition as claimed in claim 9 in which the cereal plant is wheat, barley or rye.

* * * * *